United States Patent [19]
Preston

[11] Patent Number: 5,089,234
[45] Date of Patent: Feb. 18, 1992

[54] CONTROLLED ENVIRONMENT LIQUID DILUTING AND TRANSFER VALVE ASSEMBLY

[75] Inventor: Charles R. Preston, Quakertown, Pa.

[73] Assignee: Serono-Baker Diagnostics, Inc., Allentown, Pa.

[21] Appl. No.: 391,878

[22] Filed: Aug. 9, 1989

[51] Int. Cl.$^5$ ............................................. B01L 1/00
[52] U.S. Cl. ................................. 422/103; 422/104; 137/382; 73/863.72; 73/863.73
[58] Field of Search .............. 422/103, 104, 81, 82, 422/82.12; 137/382; 220/88.3; 73/863.72, 863.73, 864.83, 864.84

[56] References Cited

U.S. PATENT DOCUMENTS

| | | | |
|---|---|---|---|
| 3,041,869 | 7/1962 | Spracklen et al. | 73/863.72 |
| 3,567,390 | 3/1971 | Rothermel | 23/253 |
| 3,863,507 | 2/1975 | Jones et al. | 73/423 A |
| 3,991,055 | 11/1976 | Godin et al. | 23/259 |
| 4,152,391 | 5/1979 | Cabrera | 422/103 |
| 4,367,645 | 1/1983 | Froment | 73/863.72 |
| 4,445,391 | 5/1984 | Cabrera | 73/864 |
| 4,507,977 | 4/1985 | Cabrera | 73/864 |
| 4,702,889 | 10/1987 | Cabrera et al. | 422/103 |
| 4,802,502 | 2/1989 | Williams | 137/554 |

Primary Examiner—Robert J. Warden
Assistant Examiner—Laura Collins
Attorney, Agent, or Firm—Parmelee, Bollinger & Bramblett

[57] ABSTRACT

A liquid diluting and transfer valve assembly of a type which includes at least a pair of valve elements with slidably or rotatable engageable surfaces which are frictionally movable relative to each other are provided with passageways therein in communication with liquids and diluents which are to be measured and transferred by the assembly. The valve assembly includes measure conduits which are arranged for selective communication with the passageways in the valve elements with the junctions of the measuring conduits and the passageways taking place at the engaged surfaces of the valve elements. This valve assembly is provided with an enclosure which completely surrounds and encloses the valve elements. The environment in the enclosure is controlled in order to inhibit evaporation and or dilute seepage of the fluids between the slidably engaged surfaces of the valve elements in order to prevent a buildup of contamination resulting in greater liquid leakage, wear and tear and breakdown in the valve assembly.

10 Claims, 5 Drawing Sheets

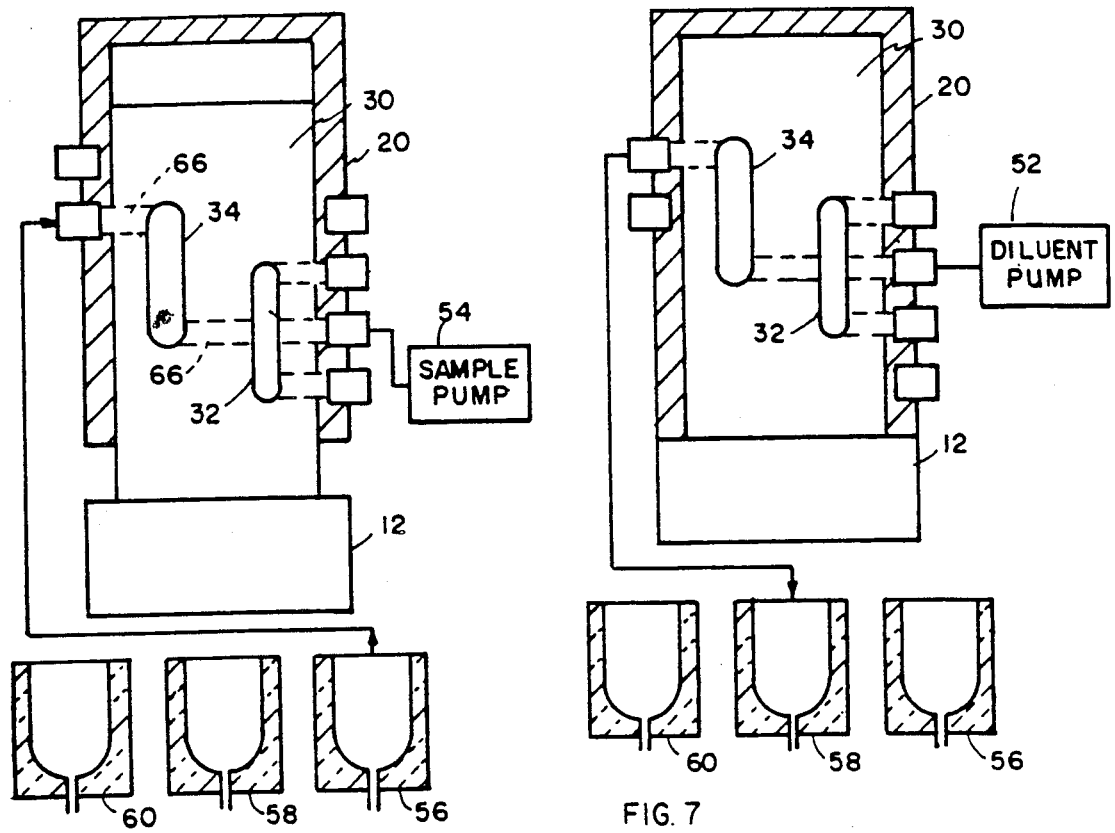
FIG. 6
FIG. 7
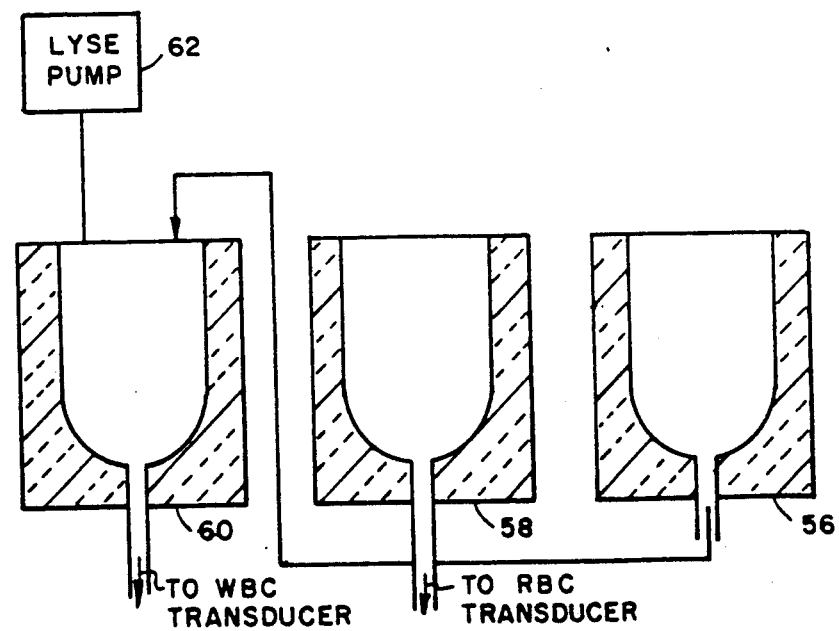
FIG. 8

CONTROLLED ENVIRONMENT LIQUID DILUTING AND TRANSFER VALVE ASSEMBLY

BACKGROUND OF THE INVENTION

This invention relates to liquid diluting and transfer valve systems, and more particularly to controlling the environment in which frictional valve faces, which do not maintain a mechanically perfect seal and rely somewhat on a filled capillary in operation, are operated in a controlled environment to inhibit breakdown caused by the imperfect seal.

Liquid transfer systems utilizing mechanically operated liquid transfer valves are useful in medicine, biology, chemistry and the like fields, in research and routine testing which is required to produce fluid mixtures of specific concentrations, accurately and automatically, and can feed known quantities of such fluids to selected locations. Such liquid transfer valve assemblies generally comprise a central element and one or more outer elements engaged against opposite faces of the central element to sandwich the central element therebetween. The central element is slidably movable with respect to the other elements between first and second positions. Measuring conduits are formed in or on one of the element and at least a pair of ports are provided in adjacent elements. Each of the ports, in one element, aligns with the port carried by the other element so that two fluid paths are defined. The central member is indexed to a first position to align one measuring conduit with one of the fluid paths for reception in that one conduit of a portion of the liquid sample. The central element is then moved to a second position and by virtue of such movement the volume of the sample in the measuring conduit is segmented and deposited in the other fluid path for combining with a diluent introduced therein so as to provide a precise dilution and, accordingly, a specific concentration of one sample.

The transfer valve assembly includes movable elements which move linearly or are rotated or both to effect the segmenting of the precise volume quantities of a sample. By providing a second conduit associated with the central member, a predetermined volume of diluent may be provided to effect a second dilution. In blood sampling, for example, the first dilution may be utilized for the purpose of making a white blood cell evaluation while a second dilution can be utilized to evaluate the red blood cell which requires substantially more dilution. The problem with these slidable frictionally engaged surfaces of the various elements of the transfer valve assemblies is that they do not form a perfect seal therebetween and are constantly being moved relative to each other causing seepage which results in a molecular layer of liquid between the sealing surfaces due to internal pressure or which layer is drawn by capillary action between the sealing surfaces as a result of surface finish porosity in the mating halves or imperfection in the flatness of the mating halves. As the volatile contents of these fluids, which are being transferred, evaporate along the interface or junction of the sealing surfaces or even more predominant on the sliding valve at the intermittently exposed ends, a residue of non-volatile solid remains forming abrasives and/or sludge. This residue results in a degradation or minute lifting of the sealing members. Either or both phenomena can contribute to increasing the flow, evaporation, residue cycle resulting in excessive outward leaking of captured fluids or inward leaking of the external environment when negative pressures are applied to the valve members. The buildup of solids at the junctions of the conduits or ports of the various elements can result in the failure of the valve assembly and at the very least requires the dismantling and removal of any evaporated residue forming on the faces of the sealing surfaces, particularly at the junctions of the ports and conduit areas.

In U.S. Pat. No. 4,702,889 a transfer valve assembly uses disk-like valve elements having frictionally engaged faces with passageways for passing both sample liquid and rinse liquid along with a continuous groove formed in one of the respective faces. The continuous groove is provided for treating the aforesaid problem by isolating the passageway openings to the faces for blocking passage of liquid material along the face to the periphery of the engaged face. Of course, the problem is that it does not stop the seepage and merely collects the seepage which still can evaporate and ultimately overflow the groove which is meant to contain it and of course must be periodically cleaned.

Whether the valve elements are pivoted, slidable or rotatable, the same problem exists and that is seepage of material between the frictionally engageable surfaces which evaporates and causes a buildup between the sealing faces of the valve elements. The present invention is directed to eliminate evaporation of such seepage and prevent a solid buildup between the faces tending to separate them more and to cause additional continuous and greater progressive buildups.

SUMMARY OF THE INVENTION

Accordingly, it is an object of this invention to provide a new and improved liquid diluting and transfer valve assembly which inhibits evaporation between the slidably engaged sealing surfaces o the transfer valve elements to prevent contamination buildup between the surfaces thereby preventing the ultimate breakdown of the valve assembly.

Still another object of this invention is to provide a new and improved transfer valve assembly which is easy to implement and simple to control.

In carrying out this invention, in one illustrative embodiment thereof, a liquid diluting and transfer valve assembly, having at least one pair of valve elements with slidably engaged surfaces which are frictionally movable relative to each other, are provided with passageways therein in communication with liquids and diluents which are to be measured and transferred by the assembly. The valve assembly includes measuring means which arrange for selective communication with the passageways in the valve elements with the junctions of the measuring means in the passageways being at the engaging surfaces of the valve elements. The improvement comprises an enclosure which completely surrounds and encloses the valve elements. The enclosure is provided with means for controlling the environment in the enclosure to inhibit evaporation of the liquids at the junctions and provide a diluting and washing effect of the seepage in the surfaces such that a buildup of contamination resulting in greater leakage, wear, tear and breakdown in the valve assembly is inhibited.

BRIEF DESCRIPTION OF THE DRAWINGS

The invention, together with further aspects, objects, advantages and features thereof will be more clearly understood, by way of example, from the following description taken in connection with of the accompanying drawings.

FIG. 6 shows the schematic of that part of FIG. 3 for aspirating the sample from the mixing container with the valve slider up.

FIG. 7 illustrates that portion of the schematic of FIG. 3 with the slider down in which a second dilution is dispensed into a red blood cell container.

FIG. 8 illustrates that portion of the schematic in FIG. 3 illustrating transferring the contents of the sample mixing container to the white blood cell container to which a lysing agent is added and dispensing the contents of the white blood cell and red blood cell containers for further testing and measuring.

DESCRIPTION OF THE PREFERRED EMBODIMENTS

The liquid diluent and transfer valve assembly which is utilized in the present invention may be referred to, at various times, as fluid transfer valve or simply valve or valve assembly which are characterized in having a movable element which is either moved linearly or rotatably or a combination of such movements to effect the segmenting of precise volume quantities of a sample. Such valves are characterized in having at least a pair of valve elements with slidably engaged surfaces which are frictionally movable relative to each other and have passageways therein in communication with liquids and diluents being measured and transferred by the valve assembly. Whether the valve elements are linearly movable, pivotable or rotatable with respect to one another, the same problem exists, namely leakage between the elements and evaporation which causes deposits to be formed between the sliding surfaces which in effect cause greater seepage, more evaporation, and a buildup of solids between the sliding surfaces which provides faulty volume measurements and/or the breakdown of the valve system. The present invention is directed to controlling the environment in which the valve operates and is described in a first embodiment in connection with a linear slidable surface type valve but it will be understood that it will be applicable to other types of valve systems, using for example, pivotal and or rotary elements as is described in a second embodiment which perform the same or similar functions, and the leakage problem which exists in such valves, is common.

Figure 1:
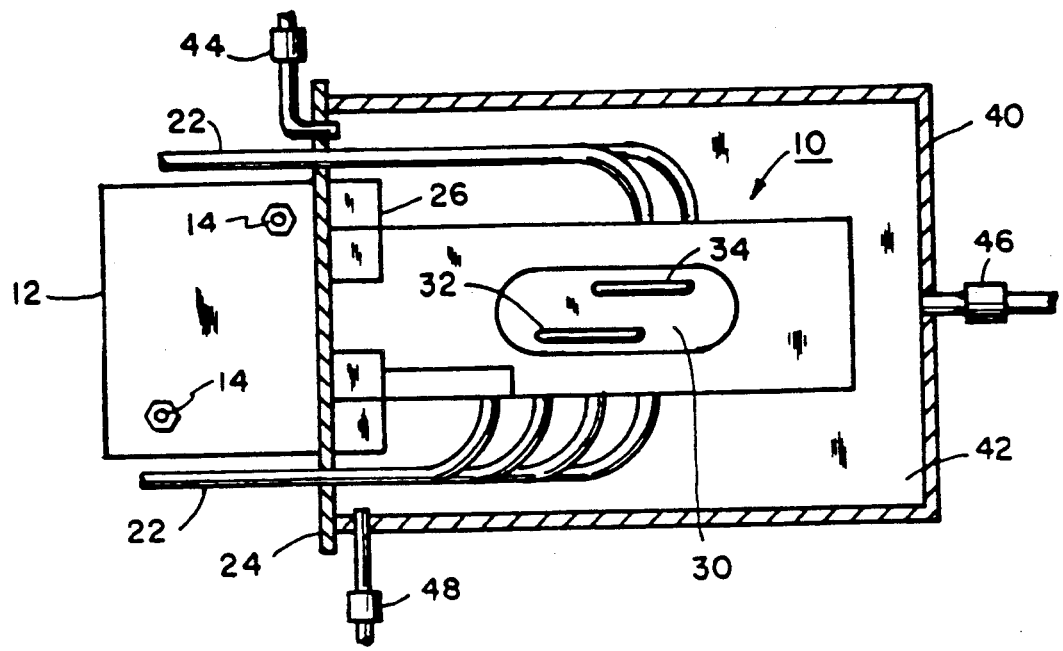
FIG. 1 is a top view of one type of liquid transfer valve assembly encased in a controlled environment in accordance with the present invention in which the enclosure is sectioned for clarity.
Figure 2:
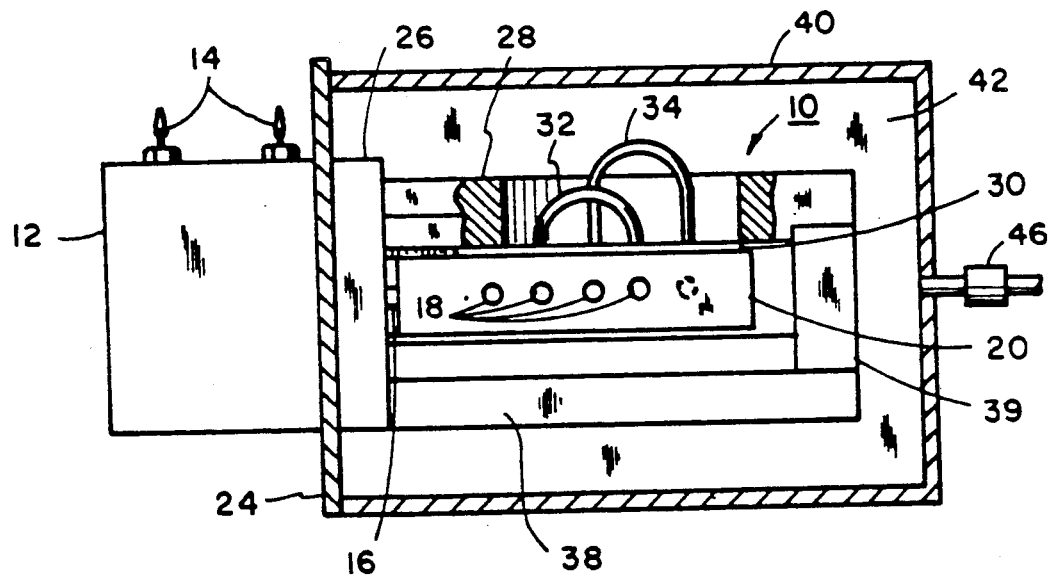
FIG. 2 is a front elevational view of FIG. 1 with the valve tubing removed and the enclosure in section as in FIG. 1.

Referring now to FIGS. 1 and 2, a transfer valve, referred to generally with the reference numeral 10, is operated by a pneumatic air-cylinder 12 through drive ports 14. The air-cylinder 12 has a drive shaft 16 coupled to and driving a slider 20 having a plurality of hollow pin terminals 18 thereon which are coupled to passageways in the slider (not shown) and to which valve tubing 22 is coupled as illustrated in FIG. 1. The air-cylinder 12 is mounted on a support plate 24 by a cylinder mounting block 26. A stator 30 is mounted on a stator support 28 which in turn is mounted to the cylinder mounting block 26. The stator 30 carries precise measurement conduits 32 and 34. The measurement conduits 32 and 34 may have different lengths and diameters and, accordingly, different volumes, for example, conduit 32 may be arranged to handle 40 microliters while conduit 34, which is longer, is designed to handle 100 microliters. A spring support 38 (springs not shown) is mounted on the lower end of the cylinder mounting block 26 and the stator support 28 and spring support 38 are linked by an end cap block 39. The valve 10 is completely enclosed by an enclosure or chamber 40 having a controlled environment 42 therein in which the valve 10 is immersed. The controlled environment 42 is under control of a fill valve 44, a drain valve 46 and an overflow valve 48.

Figure 3:
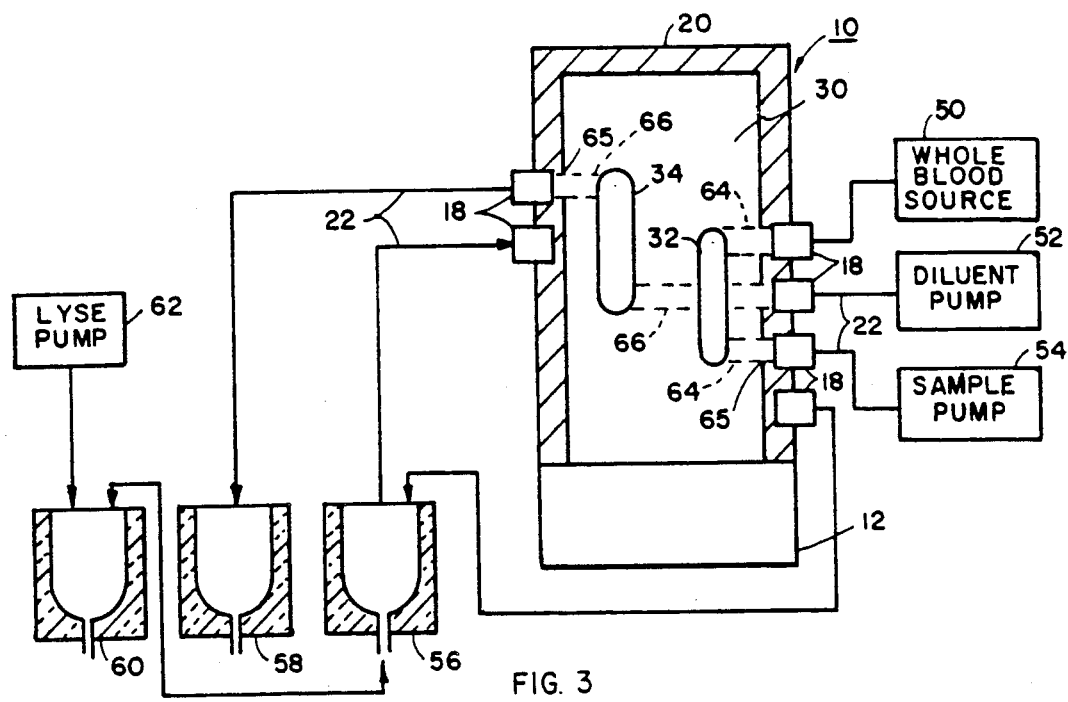
FIG. 3 is a schematic illustration of a shear valve circuit with the slider down which is used, for explanatory purposes, to illustrate one application in the use of the present invention for measuring and testing fluids useful in diagnosis, treatment and research.
Figure 4:
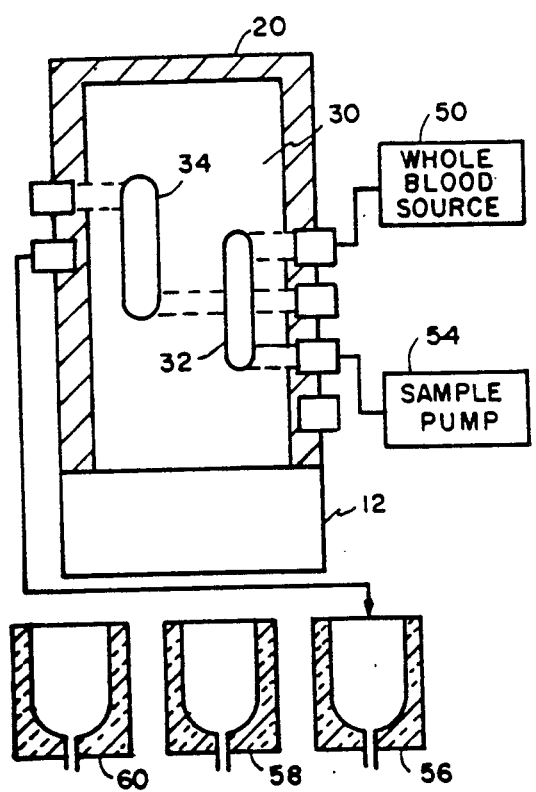
FIG. 4 shows only that part of the schematic of FIG. 3 used to aspirate a sample showing the transfer valve down.

Before discussing the controlled environment in accordance with the present invention, reference is now made to FIGS. 3 through 7 to illustrate one type of use of the transfer valve and to demonstrate the problem and the solution to the problem using the present invention. The procedure is to provide various samples for testing apparatus using samples of different dilutions and, more precisely, a first dilution which is utilized for the purpose of making white blood cell evaluations and lysing the red blood cells from the sample and for providing a second dilution to evaluate the red blood cells which requires a substantially more dilute sample. Referring first to FIG. 3 which shows in schematic form, the transfer valve 10 having the stator 30 carrying the measurement conduits 32 and 34 which are coupled by the slide 20 to various hollow pin terminals 18 to which the valve tubing 22 couples the measurements conduits to a whole blood source 50, a diluent pump 52, a sample pump 54, a sample mixing container 56, a red blood cell (RBC) container 58, and a white blood cell (WBC) mixing container 60. A lyse pump 62 is shown coupled to the WBC container 60.

The problem area with which the present invention deals is the interface region 65 between the slider 20 and the stator 30 in which passageways 64 and 66 of the measurements conduits 32 and 34, respectively, connect these conduits to the various hollow pin terminals 18. In order to illustrate the problem, a sample test is explained first with reference to FIG. 4 in which the slider 20 is down, coupling the measurement conduit 32 between the whole blood source 50 and the sample pump 54 which aspirates the sample and fills the measurement conduit 32 with a precise amount of sample.

Figure 5:
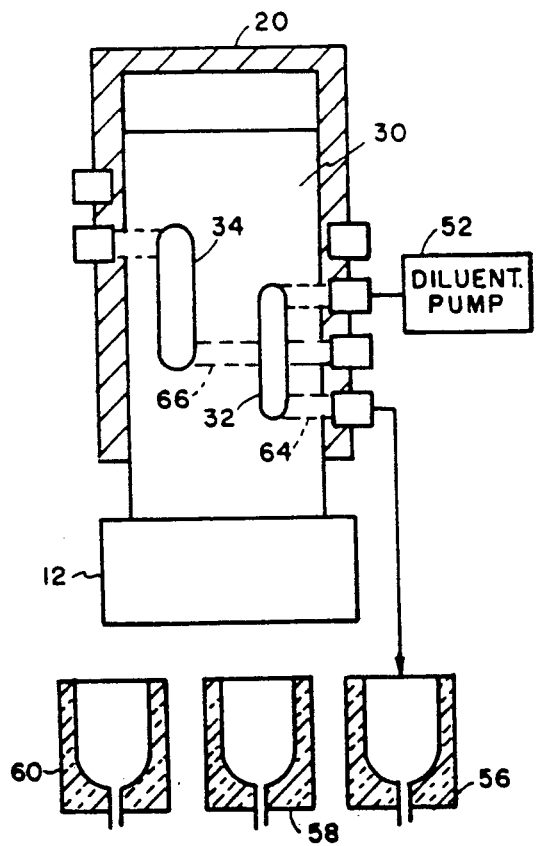
FIG. 5 illustrates the part of the schematic of FIG. 3 in which the sample and diluent are dispersed to a sample mixing container.

In step 2, as shown in FIG. 5, the slider 20 moves up connecting a diluent pump 52 to the measurement conduit 32 and the sample mixing container 56 performing the function of dispensing the sample and the diluent to the sample mixing container 56. In the next step shown in FIG. 6, with the slider 20 in the up position, the sample mixing container 56 is coupled to the measurement conduit 34 and the sample pump 54 performing the function of aspirating the diluted sample from the sample mixing container 56 to the measurement conduit 34. In the next step shown in FIG. 7, the measurement conduit 34 is coupled between the diluent pump 54 and the RBC container 58 providing a second dilution which is dispensed into the RBC container 58. In the final step, as depicted in FIG. 8, the contents of the sample mixing container 56 are transferred to the WBC container 60 where a lysing agent is added using the lyse pump 62 and the contents of the WBC and RBC containers 60 and 58, respectively, are then dispensed for further testing, for example, the contents are dispensed to particle counting transducers for counting of the WBC and RBC cells, respectively.

As will be seen from the illustrated process, the slider is sequentially moved during a series of measurement dilution and transfer functions which occurs periodically, sequentially and repeatedly during the test and measurement cycles. The problem which is encountered during the slidable movement of the elements of the valve 10 is a seepage or leakage occasioned by liquids such as blood or the diluents passing between the faces of the slider 20 and the stator 30 due to the fact that a perfect seal does not exist at the interface 65 of these valve elements which have relative movement therebetween in order to align the various passageways to supply the various samples and diluents to the measurement conduits. The resulting leakage or seepage results in a molecular layer of fluid forming due to internal pressure or by capillary action between the sealing surfaces as a result of the surface finish or porosity in the mating surfaces or imperfections in the mating surfaces. As these fluids evaporate along the interface or junction 65 of the sealing surfaces of slider and stator elements of the valve, a solid residue is formed therebetween which continues to build up thereby increasing the seepage and a buildup of the residue which results in a degradation or in minute lifting of the sealing surfaces. Either or both phenomenon can contribute to increasing the flow evaporation residue cycle resulting in excessive outward leaking of the captured fluids or the inward leaking of the external environment when negative pressure is applied to the valve 10. Now the purpose of the present invention is the minimize or eliminate the evaporation cycle and accordingly to provide a diluting of the seepage and self-cleaning of the intermittently exposed surface and the junction (interface or edges) of the sealing surfaces of the slider and stator by maintaining the valve 10 in a controlled environment 42 which is some form of stabilizing fluid. The seepage of blood sample or diluent which does get into interface has a tendency to seal the interface region and does so as long as it does not evaporate. However, when the blood sample or diluent, which in itself performs a sort of lubricant function for the sliding action in sealing at the interface region, starts to dry on the outside edges, then the dried material starts exerting pressure to push the sliding elements apart. Accordingly, the present invention prevents the evaporation cycle, and accordingly the buildup of solid materials between the sliding surfaces by immersing the valve 10 in a totally controlled environment 42 by enclosing the valve 10 in the enclosure or chamber 40. A stabilizing fluid is applied to the chamber 40 through the fill valve 44 to completely fill and submerge the valve 10 in the stabilizing fluid for preventing evaporation in the chamber. The stabilizing fluid may be any type of suitable substance in the form of a liquid, an atomized liquid or an inert gas. Deionized water is an example of a suitable substance. The chamber 40 is filled with the stabilizing fluid to prevent evaporation of the seepage from the valve 10, and furthermore to dilute such seepage so that it does not solidify but simply continues to facilitate the slidable frictional engagement between the elements of the valve. Since the process is repetitive and the environment may become somewhat contaminated with the seepage that it has been diluting, a drain valve 46 is provided in order to periodically remove the stabilizing fluid from the chamber and to refill, through the fill valve 44, the chamber 40 with a fresh supply of stabilizing fluid. The volume of stabilizing fluid, such as deionized water, which is used at any one time in the container, will depend on the frequency of cleaning. A smaller volume is required in the container on a continuous removal of the fluid from the container.

The determining factor controlling the optimum form of the stabilizing fluid is the content of the medium being transferred. In particular, a medium containing both soluble and insolubles, in general, will achieve its maximum benefit from a liquified stabilizing fluid. The fluid will act as a carrier or medium for dispersal of insoluble residue from the intermittently exposed sealing surfaces and edges while at the same time inhibit evaporation of the medium in the capillary seal thereby maintaining the soluble content in solution to prevent a buildup of undissolved solubles or abrasive crystallization formations.

In particular, a device used for precisely measuring and transferring a medium such as whole blood, containing soluble salts and protein along with insoluble cell membrane will achieve its maximum useful life utilizing a liquified stabilizing fluid environment to maintain the membrane content in its pliable state, provide a vehicle for dispersion of the membrane residue from the intermittently exposed surfaces and edges, and preventing evaporation of the transfer medium thereby inhibiting the soluble content from leaving solution.

In contrast, the useful life of a device measuring and transferring a medium containing solubles only, can be significantly extended through the use of a liquified stabilizing fluid or by maintaining the environment in a saturated state through the use of a stabilizing fluid in the form of an atomized liquid or inert gas to prevent evaporation of the transferred medium. More specifically, any compatible fluid with a density greater than the density of the medium's vapors at the maximum operating temperature will prevent evaporation of the medium thereby maintaining the medium's soluble content in solution rather than solidifying and causing a buildup or abrasive crystal formation on the sealing surfaces.

Figure 9:
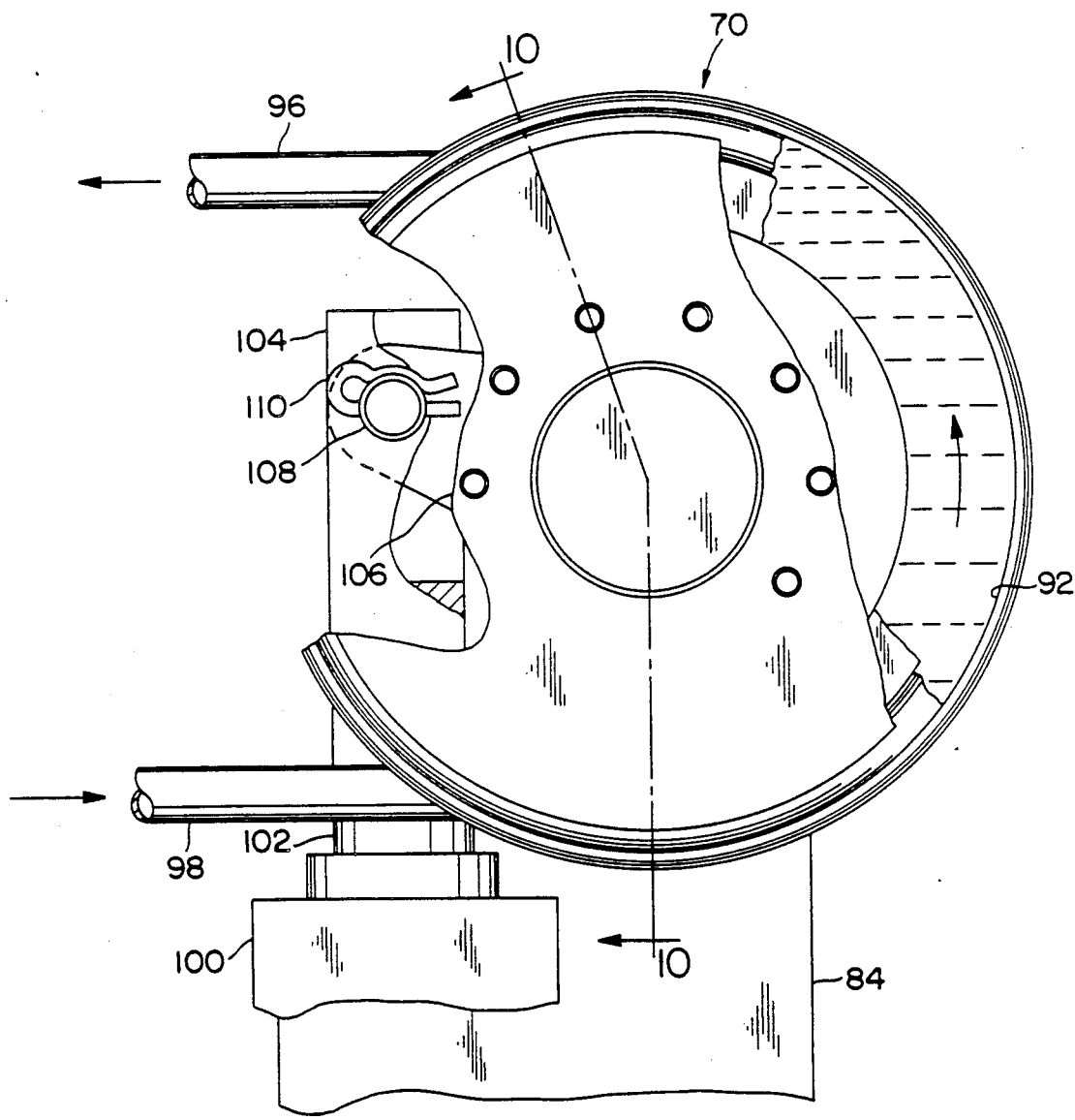
FIG. 9 is a view partially broken away of a rotary liquid transfer valve encircled in a controlled environment in accordance with another embodiment of the present invention.
Figure 10:
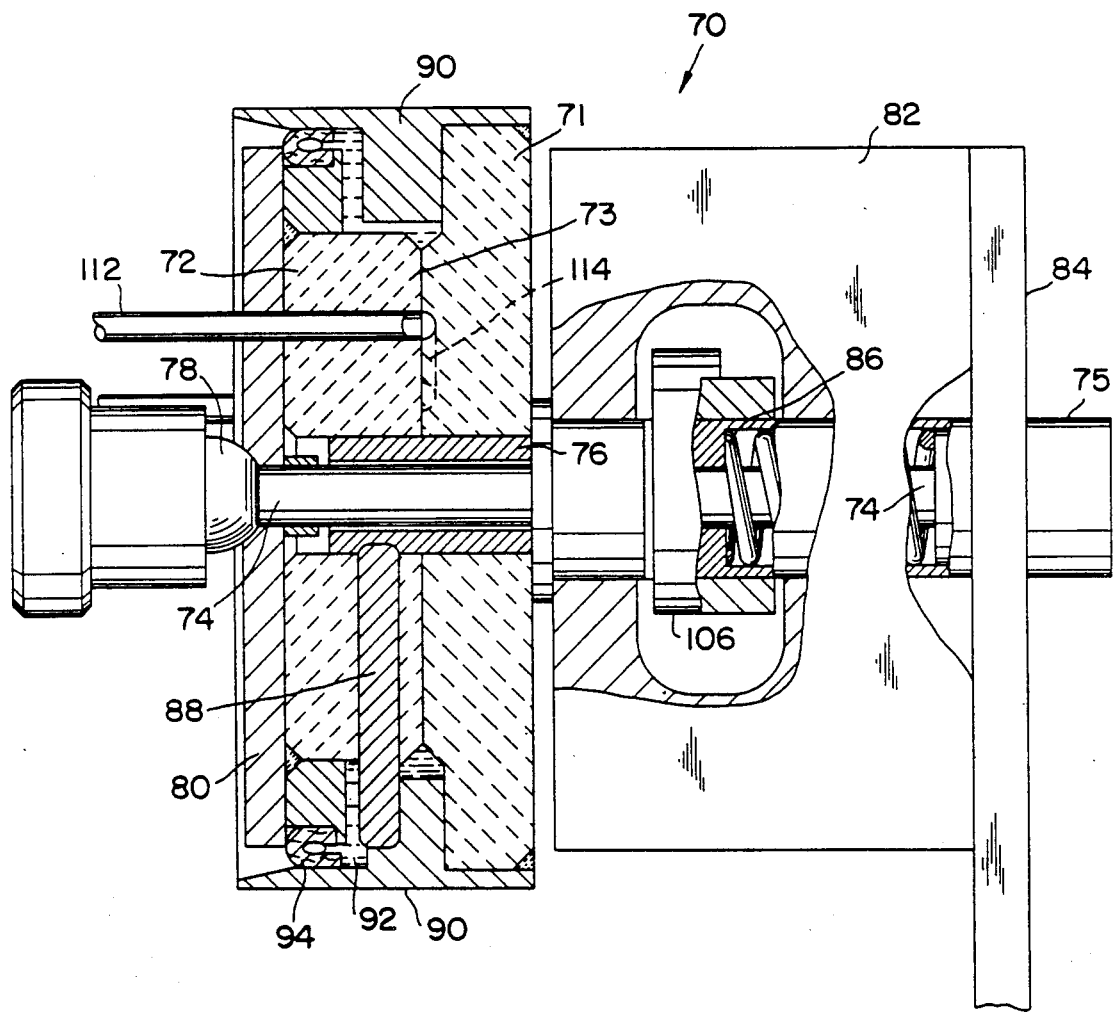
FIG. 10 is a side elevational view partially in section of the rotary liquid transfer valve of FIG. 9.

A rotary embodiment of the present invention is illustrated in FIGS. 9 and 10 in which the rotary shear valve is referred to generally with the reference numeral 70. The rotary valve 70 comprises a rotor 72 and a stator 71 mounted on a shaft assembly 75 having an outer shaft 76 and an inner shaft 74. The inner shaft 74 runs through a ball pivot 78 which bears on a plate 80. The shaft assembly 75 is positioned in a block 82 mounted on a mounting plate 84. A spring 86 positioned in the outer shaft 76 surrounding said inner shaft 74, spring loads the shaft assembly 75 which urges the rotor 72 and the stator 71 together at interface 73. The rotor 72 is affixed to the inner shaft 74 by a drive pin 88. A water jacket 90 completely surrounds the interface 73 between the rotor 72 and the stator 71 forming a reservoir 92 having a seal 94. Tubes 96 and 98 are connected to jacket 90 for flushing the reservoir 92.

As will be seen in FIG. 9, the valve 70 is operated by an air cylinder 100 having piston 102 carrying a yoke 104 for driving a pivot arm 106 which is coupled to the yoke 104 by a clevis pin 108 fastened therein by a hair pin clip 110.

As will be seen in FIG. 10, a sample tube 112 is provided for feeding a blood sample to a sample loop 114 (shown in phantom) in the stator 71. The rotor contains several loops (not shown) which are designed to communicate with the sample loop to deliver blood samples through the sample loop 114. Since the invention does not reside in the aspiration, dilution and sample and resample steps which have already been described, only a general description will now be undertaken. The rotary embodiment shown in FIGS. 9 and 10 is referred to as a shear valve because it contains a rotor 72 and a stator 71 which shift from a sample position (aspiration) to a dilute/resample position and then back in normal operation. The shifting of the relative positions of the rotor 72 with respect to the stator 71 by actuation of the air cylinder 100 allows the valve 70 to shear away a known volume of blood sample contained in the sample loop 114 in the stator 71. After shearing a diluent port in the rotor 72 (not shown) is positioned at one end of the blood filled sample loop 114 which delivers a known volume of diluent to flush the blood sample out of the loop to mixing bowls to complete the first dilution. In this same position, the valve ports are aligned to resample a portion of the first dilution through a second loop of tubing (not shown) which holds the resampled fluid until the rotor 72 shears back to the initial sample position by the activation of the air cylinder 100. Then the resampled fluid is flushed through with more diluent to effect a second dilution for reasons previously described in connection with the embodiment in FIGS. 1 and 2.

Again, as in the case of the embodiments of FIG. 1, seepage of fluid at the interface 73 is always present at or near the outer periphery of the valve due to capillary action. The seepage is the saline diluent having traces of blood. Evaporation of the seepage produces deposits of dried salts and blood that can leave the valve 70 and can possibly be aspirated by the operator or others in the vicinity subjecting such individuals to any blood borne diseases that may be present in the samples being tested. As in the other embodiment, the seepage causes a buildup of deposits across the interface 73 gradually increasing friction between the rotating surfaces which could cause the valve to lock requiring frequent disassembly and cleaning. The water jacket 90 which forms a fluid reservoir around the interface 73 eliminates both of the aforesaid concerns. Controlling the environment when the shearing action takes place effectively handles the problem of seepage by continuously cleaning or removing any seepage or buildup of residue.

The operation of the transfer valve of any type, whether having linearly slidable, pivotally or rotatably slidable elements, prolongs the life of the valve and permits more measurements to be run on various samples without breakdown or the requirement of shutting down the system to clean the valve elements. Accordingly, the testing process is enhanced by extending the life of the valves as well as permitting a greater number of tests with less down time or equipment cleaning or repairing.

Since other changes and modifications, varied to fit particular operating requirements and environments, will be apparent to those skilled in the art, the invention is not considered limited to the examples chosen for purposes of illustration, and includes all changes and modifications which do not constitute a departure from the true spirit and scope of this invention as claimed in the following claims and equivalents thereto.

I claim:

1. In a liquid diluting and transfer valve assembly which includes at least a pair of valve elements with slidably engaged surfaces which are frictionally movable relative to each other with an interface therebetween, said valve elements having passageways therein for communication of liquid being measured and transferred in said assembly, wherein the passageways in one of said valve elements are capable of being selectively brought into fluid communication with the passageways in the other of said valve elements at the interface of said engaged surfaces, the improvement comprising an enclosure completely surrounding and enclosing valve elements for retaining a stabilizing fluid therein so as to inhibit evaporation of and dilute seepage of liquids between engaged surfaces to prevent buildup of contamination therebetween.

2. A liquid diluent and transfer valve assembly as claimed in claim 1 wherein said enclosure has a fill valve for filling said enclosure with said stabilizing fluid.

3. A liquid diluting and transfer valve assembly as claimed in claim 1 wherein said enclosure has a drain valve for draining said stabilizing fluid therefrom.

4. A liquid diluting and transfer valve assembly as claimed in claim 1 wherein said stabilizing fluid is a liquid.

5. A liquid diluting and transfer valve assembly as claimed in claim 1 wherein said stabilizing fluid is water.

6. A liquid diluting and transfer valve assembly as claimed in claim 1 wherein said valve elements comprise a rotor and a stator with rotatably slidably engaged surfaces with an interface therebetween and said enclosure comprises a jacket forming a reservoir which completely surrounds said interface, said reservoir adapted to retain said stabilizing fluid therein.

7. In a liquid diluting and transfer valve assembly which includes at least a pair of valve elements with slidably engaged surfaces which are frictionally movable relative to each other with an interface therebetween, said valve elements having passageways therein for communication of liquid being measured and transferred in said assembly, wherein the passageways in one of said valve elements are capable of being selectively brought into fluid communication with the passageways in the other of said valve elements at the interface of said engaged surfaces, the improvement comprising a stabilizing fluid filled enclosure completely surrounding and enclosing valve elements for retaining the stabilizing fluid therein so as to inhibit evaporation of and dilute seepage of liquids between engaged surfaces to prevent buildup of contamination therebetween.

8. In a blood diluting and transfer valve assembly for handling blood sample mixtures, which valve assembly includes a pair of valve elements with slidably engaged surfaces which are frictionally movable relative to each other with an interface therebetween, said valve elements having passages therein for communication of blood sample and diluent being measured and transferred in said assembly, wherein the passageways in one of said valve elements are capable of being selectively brought into fluid communication with the passageways in the other of said valve elements at the interface of said engaged surfaces, the improvement comprising a stabilizing liquid filled enclosure completely surrounding and enclosing valve elements for retaining a stabilizing liquid therein, which stabilizing liquid controls the environment in the enclosure and inhibits evaporation of and dilutes seepage of blood between engaged surfaces to prevent buildup of contamination therebetween.

9. A blood diluting and transfer valve assembly as claimed in claim 8 wherein the stabilizing liquid is water and said enclosure has:
 a fill valve for filling said enclosure with the stabilizing liquid, and
 a drain valve for draining said stabilizing fluid from said enclosure.

10. A blood diluting and transfer valve assembly as claimed in claim 9 wherein said valve elements comprise a rotor and a stator with rotatably slidably engaged surfaces with an interface therebetween and said stabilizing liquid filled enclosure comprises a jacket forming a reservoir which completely surrounds said interface, said reservoir retaining said stabilizing liquid therein.

* * * * *